(12) United States Patent
Cornier

(10) Patent No.: US 12,053,362 B2
(45) Date of Patent: Aug. 6, 2024

(54) DEVICE FOR THE EXTERNAL SUPPORT OF THE FEMALE URETHRA UNDER STRESS

(71) Applicant: EURL CORNIER, Paris (FR)

(72) Inventor: Edgard Cornier, Paris (FR)

(73) Assignee: EURL CORNIER, Paris (FR)

( * ) Notice: Subject to any disclaimer, the term of this patent is extended or adjusted under 35 U.S.C. 154(b) by 884 days.

(21) Appl. No.: 17/143,295

(22) Filed: Jan. 7, 2021

(65) Prior Publication Data

US 2021/0220106 A1 Jul. 22, 2021

(30) Foreign Application Priority Data

Jan. 17, 2020 (FR) ........................ 2000430
Nov. 17, 2020 (FR) ........................ 2011794

(51) Int. Cl.
| | | |
|---|---|---|
| A61F 2/00 | (2006.01) |
| A41B 9/00 | (2006.01) |
| A41B 9/14 | (2006.01) |
| A61F 5/24 | (2006.01) |
| A61F 5/28 | (2006.01) |
| A61H 1/00 | (2006.01) |
| A61H 39/04 | (2006.01) |

(52) U.S. Cl.
CPC ............ *A61F 2/0009* (2013.01); *A41B 9/004* (2013.01); *A41B 9/14* (2013.01); *A41B 2400/32* (2013.01)

(58) Field of Classification Search
CPC . A61F 2/0009; A61F 5/24; A61F 5/28; A41B 9/004; A41B 9/14; A41B 2400/32; A61H 2201/0157; A61H 2201/163; A61H 2201/1652; A61H 1/008; A61H 39/04
See application file for complete search history.

(56) References Cited

U.S. PATENT DOCUMENTS

| | | | | |
|---|---|---|---|---|
| 4,577,591 A | * | 3/1986 | Wesseldine | ............ A01K 23/00 |
| | | | | 119/869 |
| 2015/0034074 A1 | * | 2/2015 | Tripolsky | .................. A61F 5/28 |
| | | | | 128/98.1 |

* cited by examiner

*Primary Examiner* — Thaddeus B Cox
*Assistant Examiner* — Joshua Daryl D Lannu
(74) *Attorney, Agent, or Firm* — Renner Kenner; Arthur M. Reginelli

(57) ABSTRACT

Device for external directional support of the female urethra under stress, consisting of a rigid cushion (1) fixed to a rigid counter-support (2) placed in the rear part of a belt or briefs, and comprising a partial rear perineal support part, the rigid counter-support (2) being connected at the front by adjustable straps (2) supporting it to a belt (5) or briefs whose rear periphery is rigidified by an insert or other non-folding material.

1 Claim, 9 Drawing Sheets

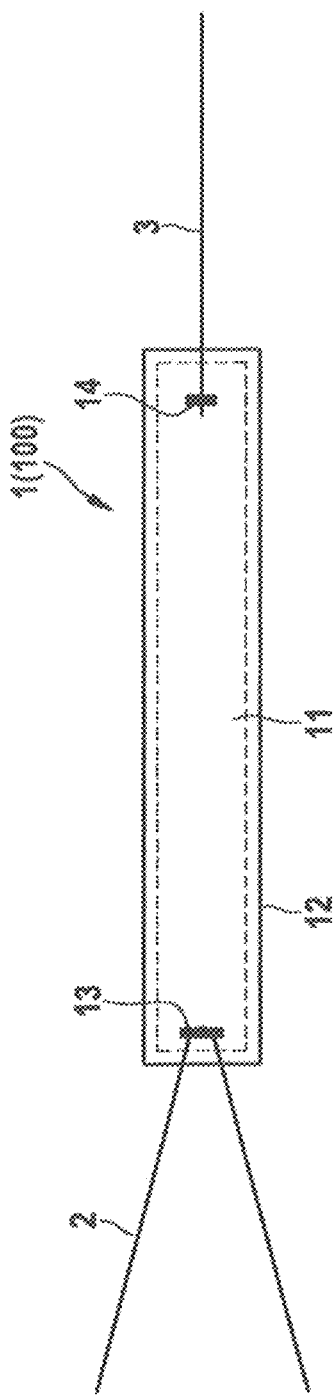

The Arrow shows the direction of the quasi static displacemet caused by pressure in the parabolic shape of the pelvis (http://perineologie-vectorielle.com). The perineum reflects forces upward to the Pubic Bone.

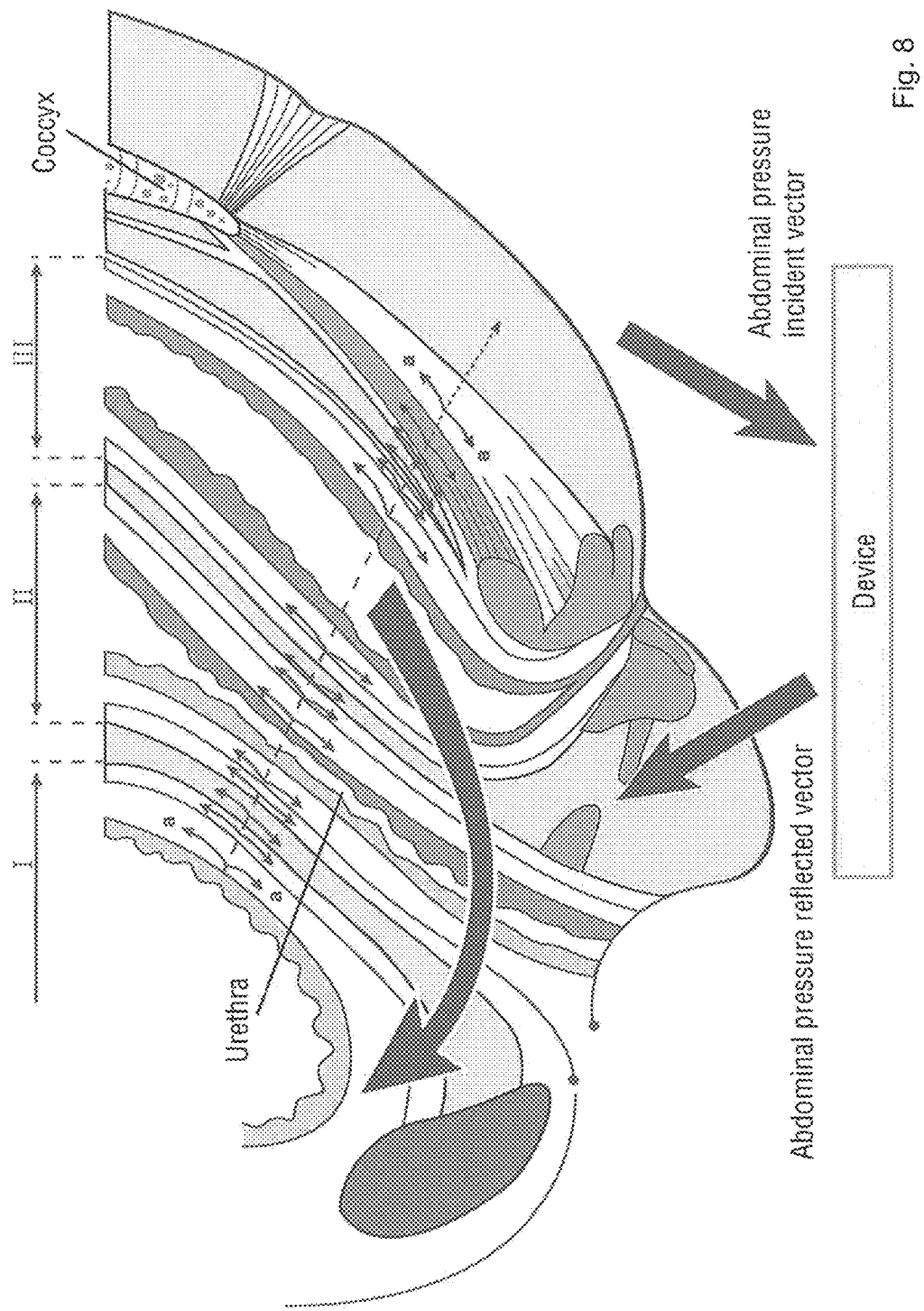

DEVICE FOR THE EXTERNAL SUPPORT OF THE FEMALE URETHRA UNDER STRESS

FIELD OF THE INVENTION

The present invention refers to a device for externally maintaining the female urethra under stress.

According to a new postulate (http://perineologie-vectorielle.com) developed by the inventor, the abdominal forces are not directed vertically to the pelvic floor. They are reflected from the bone surface and muscle structure of the small pelvis. These forces are physically redirected forward. Friction between tissues bonded together is retained by the young connective tissue. (reference A2499EC European Journal of Obstetrics & Gynecology and Reproductive Biology 234 (2019)—From tissue viscoelasticity to vectorial perineology—Edgard Cornier 1, 2,*et al.) the pressures produce quasi-static plicature movements between the organs. The plicature of the organs creates areas called "functional" areas. These areas obstruct leakage. The invention consists in correcting these force returns to recreate the functional plicature of the organs of the small pelvis. A posterior support used with the redirection of these force vectors, will allow the flexion of the female urethra, its closure, and the healing of urinary stress incontinence. The remainder of the pelvis, both centrally and laterally (the labia majora and adjacent tissues) should not be retained and should remain free to move.

STATE OF THE TECHNIQUE

Approximately 20% of young women and 77% at the age of tissue sagging suffer from urinary incontinence disorders (Urinary Incontinence in Women: A Review. Lukacz E S, Santiago-Lastra Y, Albo M E, Brubaker L.JAMA. 2017; 3; 24(318): 10-1604.)

The available therapeutic tools are few and most affected women are obliged to resort to wearing absorbent diapers.

Muscle re-education alone is not very effective in the long term and can be restrictive. It needs supplementing by different methods, calling for a personal investment that is difficult to handle in the long term. Stopping training is accompanied by recurrence.

Kegel Exercises, Biofeedback, Electrostimulation, and Peripheral Neuromodulation Improve Clinical Symptoms of Fecal Incontinence and Affect Specific Physiological Targets: A Randomized Controlled Trial. Mundet L, Rofes L, Ortega O, Cabib C, Clavé P. J Neurogastroenterol Motil. 2020 October The use of intra-vaginal pessaries is uncomfortable, poorly monitored, and not very effective on bladder weakness. Pessary use in stress urinary incontinence: a review of advantages, complications, patient satisfaction, and quality of life. Al-Shaikh G, Syed S, Osman S, Bogis A, Al-Badr A.Int J Womens Health. 2018 Surgery is often used to insert a direct suburethral support sling to cause forced flexion of the urethra, to close it under stress. This surgery has been widely used by Urologists. But the high percentage of complications has now outlawed or very strongly restricted its use, (Survey on surgery for stress urinary incontinence in an era mid-urethral slings are being questioned. D'hulster AS, Housmans S, Spaans W, Van der Aa F, Slabbaert K, Milani A L, Deprest J.Int Urogynecol J. 2020 April; 31(4): 695-702).

The following documents cover the support of the whole perineum according to the technological background: EP 2 158 882, US 2015/034074, JP 2014 1510-20. These earlier patents propose devices placed over the entire perineum and held in place by straps. They are designed to prevent prolapse displacement by pushing it in general, using a convex or concave device, towards the inside of the whole perineum.

These devices tend to be wide, bearing on the outside of the vulva, on the labia majora. They sometimes have a gutter in front to provide an outlet for urine. None of them claims to be a treatment for bladder weakness in women.

These devices lift all the organs of the small pelvis far beyond the posterior area of the perineum and lift all the pelvic tissues. They are designed to control large organ prolapses. They have no plicature effect. As a result, they may even aggravate bladder weakness once again. (Reference: Commentary on 'De novo urinary incontinence after pelvic organ prolapse surgery-a national database study'. Abdelrahman A.Int Urogynecol J. 2020 Feb. 31(2):309)

SUMMARY OF THE INVENTION

The present invention aims at developing a directional device that forces the urethra to flex. This allows the plication of the urethra during an abdominal effort because of a partial and posterior support.

Accordingly, the invention refers to a device for externally maintaining the female urethra under stress, characterized in that it comprises
- a rigid rectangular cushion with a back strap and two front straps and covering the posterior part of the perineum.
- an abdominal belt with one rear and two front attachment points which adjustably receive respectively the one rear and two front straps to hold the rigid cushion against the rear and lower perineal area, starting from the coccyx.

The directional support device according to the invention is able to redirect the abdominal pressure forces during abdominal effort thanks to the rear placement of this rigid, flat and narrow counter-support, placed in front of the coccyx, not covering the entire perineal surface area and remaining at some distance from the urinary orifice. It allows the occlusive plication of the functional area of the urethra, or for vesico urethral angulation and closure.

In one embodiment, the belt has a rear reinforcement supporting the rear attachment point.

In another embodiment, the belt is combined with briefs and in particular the rigid cushion is integrated in the intermediate part of the briefs connecting the front and back parts.

The briefs have a reinforced rear part at the waistband supporting the rear attachment point and a rigid rear part connected to the reinforcement of the gluteal cleft part of the briefs.

Another advantageous characteristic is that the briefs have a double wall at the front, forming a passage route for each of the front straps to reach the two adjustable attachment points on the front sides.

Advantageously, the front adjustable attachment points each consist of a double ring over the exit opening of the corresponding strap. This embodiment allows easy and simple adjustable fastening.

Advantageously, the rear adjustable attachment point includes a through buckle attached to the rear reinforcement and the strap has a toothed snap end for hooking the strap into one of the teeth of the buckle to complete a fixed adjustment.

Once secured, this adjustment is maintained while the adjustment at the front attachment points continues to be possible, allowing tightening or loosening at any time depending on the need or to cater to comfort.

Particularly advantageously, the rigid cushion is integrated in the rear lower region of the intermediate part of the briefs, while the front of the cushion has the two straps passing through the two routing channels of the double front wall to join the two front attachment points.

This embodiment is particularly advantageous because it is practical and comfortable.

The average dimensions of the rigid cushion are of the order of: length from 5 cm to 11 cm and width of 2 cm.

A flexible envelope comprising a biocompatible protection surrounds the rigid part, consisting of the panel.

The rigid panel comprises a device or ring at each end to connect it to the rear strap and the two front straps. These straps are connected to a single belt or combined/integrated with briefs.

The belt or the briefs comprise an insert or a piece of rigid material in the back.

In brief, the waistband forming a belt, or the briefs are painlessly placed over the gluteal cleft relief at the iliac wings. The waistband or briefs are reinforced in their rear third by an insert preventing the waistband or the waistband of the briefs from giving under tension.

In this way, overall comfortable support the whole ensemble is provided.

BRIEF DESCRIPTION OF THE DRAWINGS

This invention is described in greater detail below by means of the design methods shown in the attached drawings, in which:

FIG. 1 schematic plan view of the rigid cushion.

DESCRIPTION OF ILLUSTRATIVE EMBODIMENTS

Figure 2A:
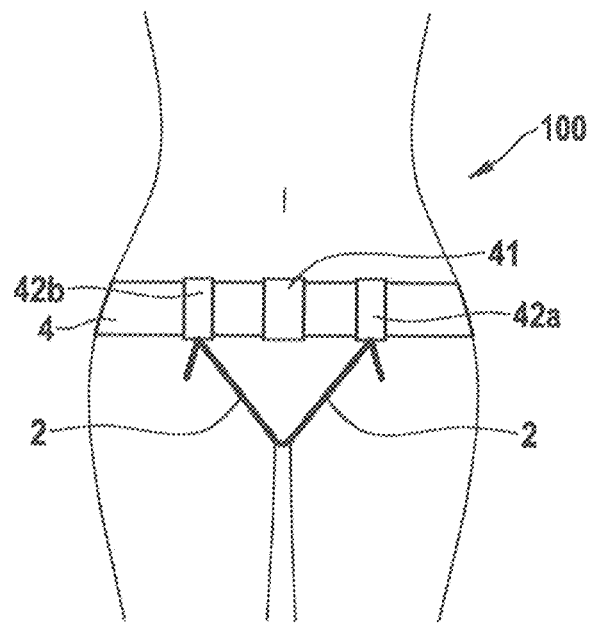
FIG. 2A front view of the entire cushion device installed according to a first embodiment.

The schematic top view of FIG. 1 shows a cushion 1 according to the invention consisting of a rigid panel 11 housed in a flexible envelope 12. The panel is equipped with a front attachment 13 and a rear attachment 14. The rear attachment 14 is fitted with a rear strap 2 and the front attachment is fitted with two front straps 3.

The rigid panel is about 5 to 11 cm long and about 2 cm wide. The flexible envelope 12 enclosing the rigid panel is a free envelope or a fixed envelope or is integrated to the panel 11.

According to one embodiment, cushion 1 is made by two-part injection of two plastics, with a relatively rigid material forming the insert 11 and a biocompatible flexible material forming the envelope 12.

Figure 2B:
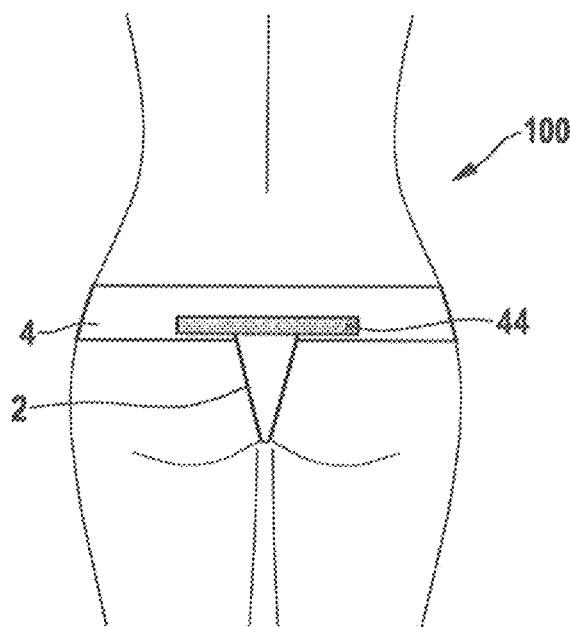
FIG. 2B rear view

The external directional support device 100 according to the invention comprises a cushion 1 as shown in FIG. 1 and a belt 4 as shown in FIGS. 2A and 2B.

Belt 4 is a wide, elastic belt with an optional 41 fastener for its adjustment. At the front, the belt 4 has two attachment points 42a, 42b, and at the rear a rear attachment point 43 attached to a rear reinforcement 44.

FIG. 2A shows the two front straps 2, connected to each other at the attachment points 42a, 42b respectively, diverging in a V-shape.

FIG. 2B shows the rear strap 3, connected to the rear attachment point 43. The front straps are preferably elastic and rise towards the waistband, spreading out along the folds of the groin and through the belt 4. They allow tension adjustment at any time while the support device 100 is being worn.

In brief, the waistband 4 is painlessly placed over the gluteal cleft relief at the iliac wings. The waistband formed by the belt 4 is reinforced in its rear third by a reinforcement 44 preventing the belt from sagging when under tension to allow the comfortable wearing of the entire support device 100.

Figure 3:
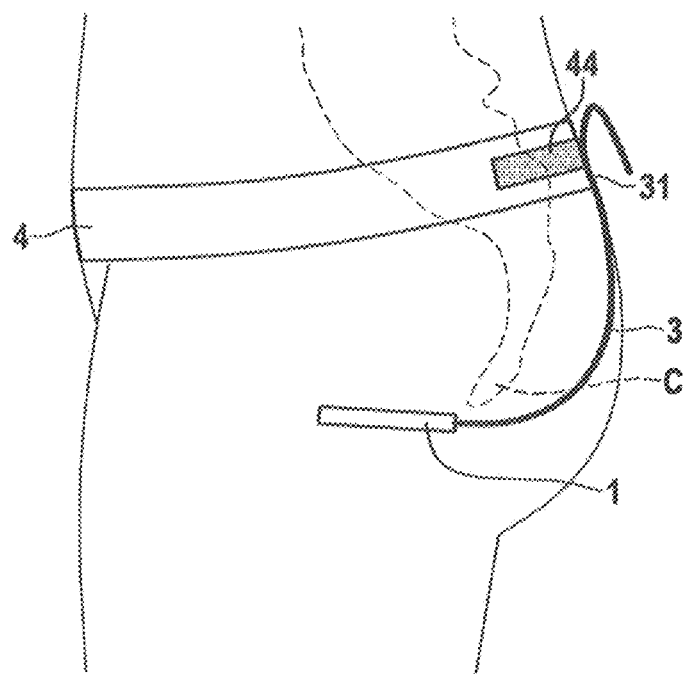
FIG. 3 schematic view of the rectangular cushion and belt at the rear attachment point FIG. 4A detail view of a rear attachment embodiment FIG. 4B detail view of two front attachment points according to one embodiment of the invention FIG. 5 perspective view of a first embodiment of the briefs FIG. 6A front view of another embodiment of the briefs with an integrated cushion FIG. 6B view of the intermediate part of the briefs in FIG. 6A FIG. 6C rear view of the briefs in FIG. 6A FIG. 6D view of the double front wall FIG. 7 anatomical diagram of the small pelvis showing the vectorial return of the forces in the small pelvis on the perineum FIG. 8 anatomical diagram showing the complementary transmission of forces by a retaining device according to the invention placed under the back of the perineum.

The anatomical diagram in FIG. 3 schematically depicts the positioning of belt 4 with its rear reinforcement 44 and the rear attachment point. Cushion 1 is installed in front of the coccyx C.

Figure 4A:
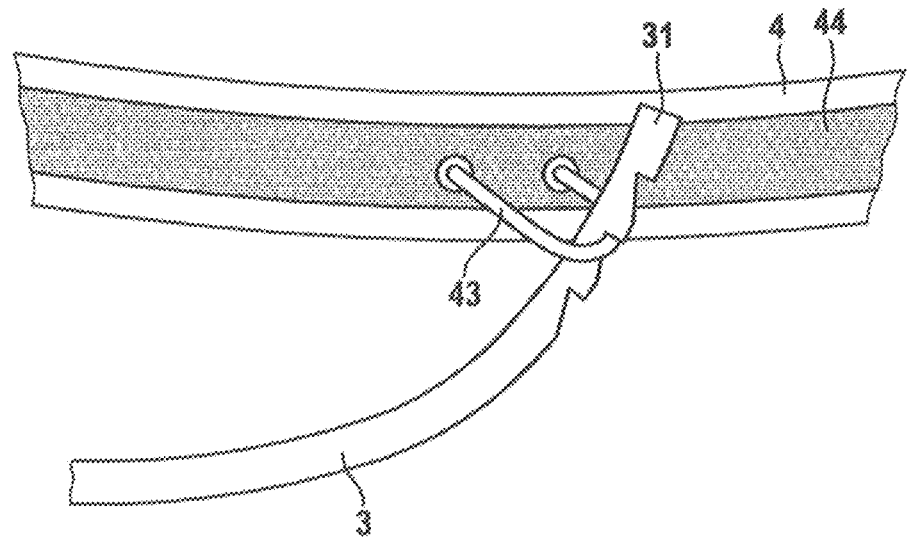

FIG. 4A shows an embodiment of the rear attachment point 43 and the rear strap 3, provided with teeth to form a rack-like arrangement for adjustable attachment in the buckle formed by the rear attachment point 43 connected to the reinforcement 44 of the belt 4. Rear adjustment is made after the belt 4 is put on. The adjusting device consists of the combination of the ring 43, reinforcement 44 and the toothed part at the end of the rear strap 3. This adjustment remains fixed once made. Thus, the rear end of cushion 1 is placed permanently against the coccyx C.

Figure 4B:
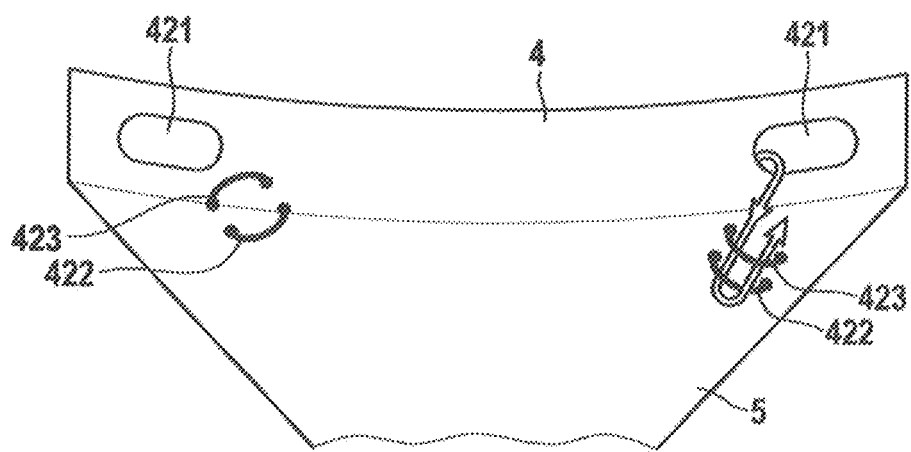

FIG. 4B shows the two front attachment points 42a, 42b of the belt 4 shown here integrated into briefs 5.

The belt has two holes 421 for the passage of the front straps 2 on the right and on the left and, at these holes, two coupled rings 422, 423 allowing the front strap 2 to pass in an S-shape through the first ring 422 and then around the second ring 423 so that the two loops of strap 2 are locked between the two rings 422, 423 by the pull of strap 2 connected to the front end of the cushion 1.

Figure 5:
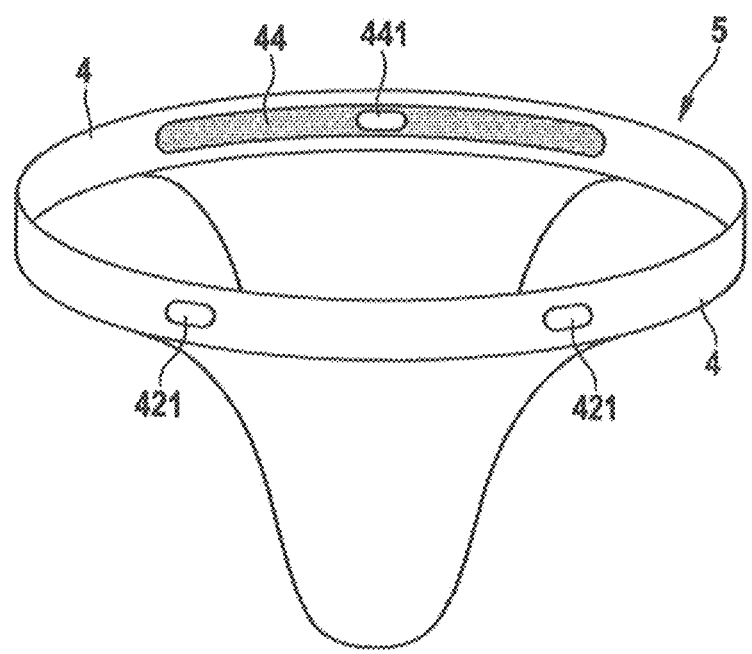

FIG. 5 is a highly schematic perspective view of a belt 4 integrated with briefs 5. Belt 4 has the structure described above with two holes 421 at the front for the passage of the front straps 2 and at the rear a reinforcement 44 with a hole 441 for the passage of the rear strap 3. This opening 441 can be made in the reinforcement 4 or in the rear part of the briefs below the waistband 4.

The rear attachment point 43 on the outside the belt 4 is not visible in FIG. 5.

Figure 6A:
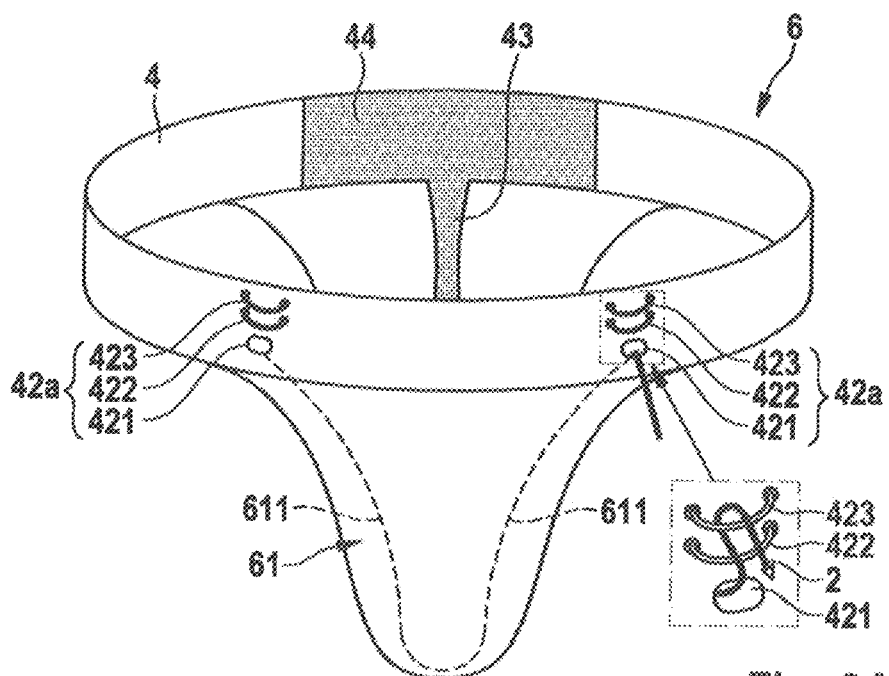
Figure 6B:
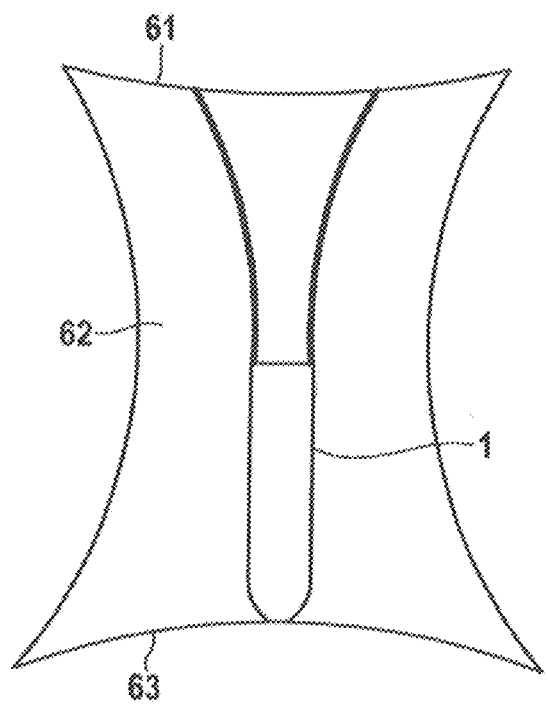
Figure 6C:
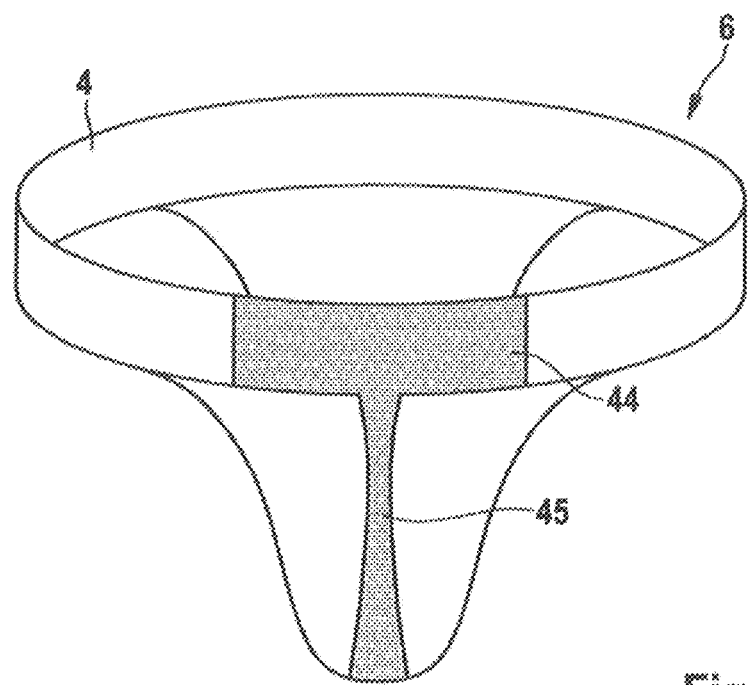

FIGS. 6A, 6B, 6C show another embodiment of briefs 6 integrating cushion 1 into the briefs and thus combining to form the external directional support device 100 according to the invention.

FIG. 6A is a perspective view of the front 61 of briefs 6 with belt 4 corresponding to the embodiments described above.

FIG. 6B shows the integration of cushion 1 in the intermediate part 62 of briefs 6. Cushion 1 supports the two front straps 2. At the back (FIG. 6C) briefs 6 have an integrated reinforcement in the rear part 63 of the briefs, connected to the belt 4 and its reinforcement 44 and extension 45.

Figure 6D:
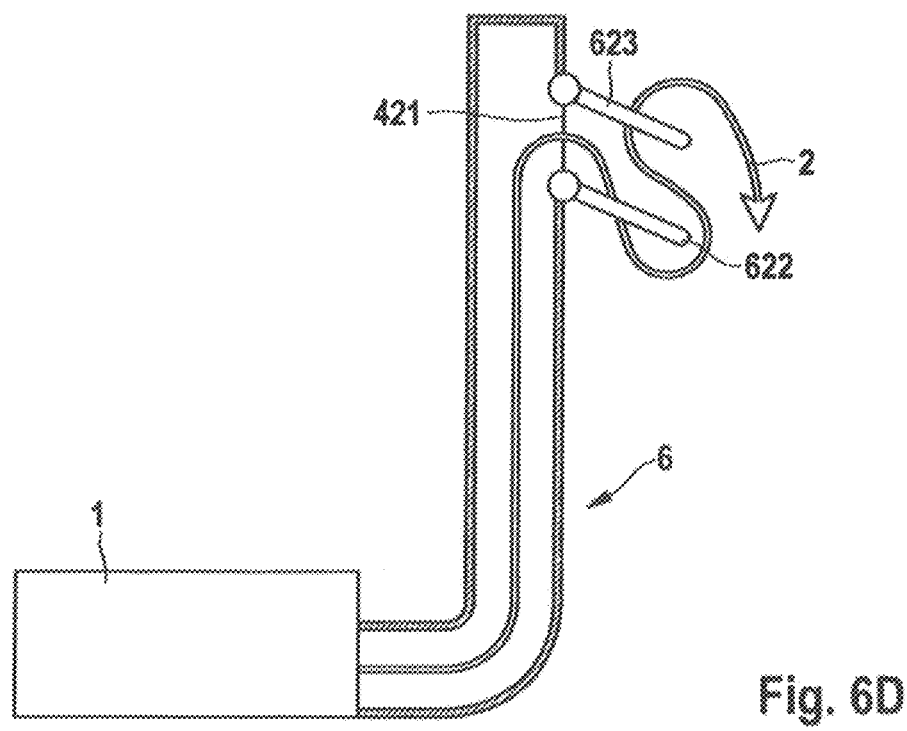

The two front straps 2 run through the double front wall of the briefs in two channels 611 opening out under or at waistband 4, near the two rings 42a, b. The front straps 2, not shown in FIG. 6A, extend through the two holes 421 to enclose the two loops 422, 423 of each front attachment point 42a,b. (see also FIG. 6D).

Figure 7:
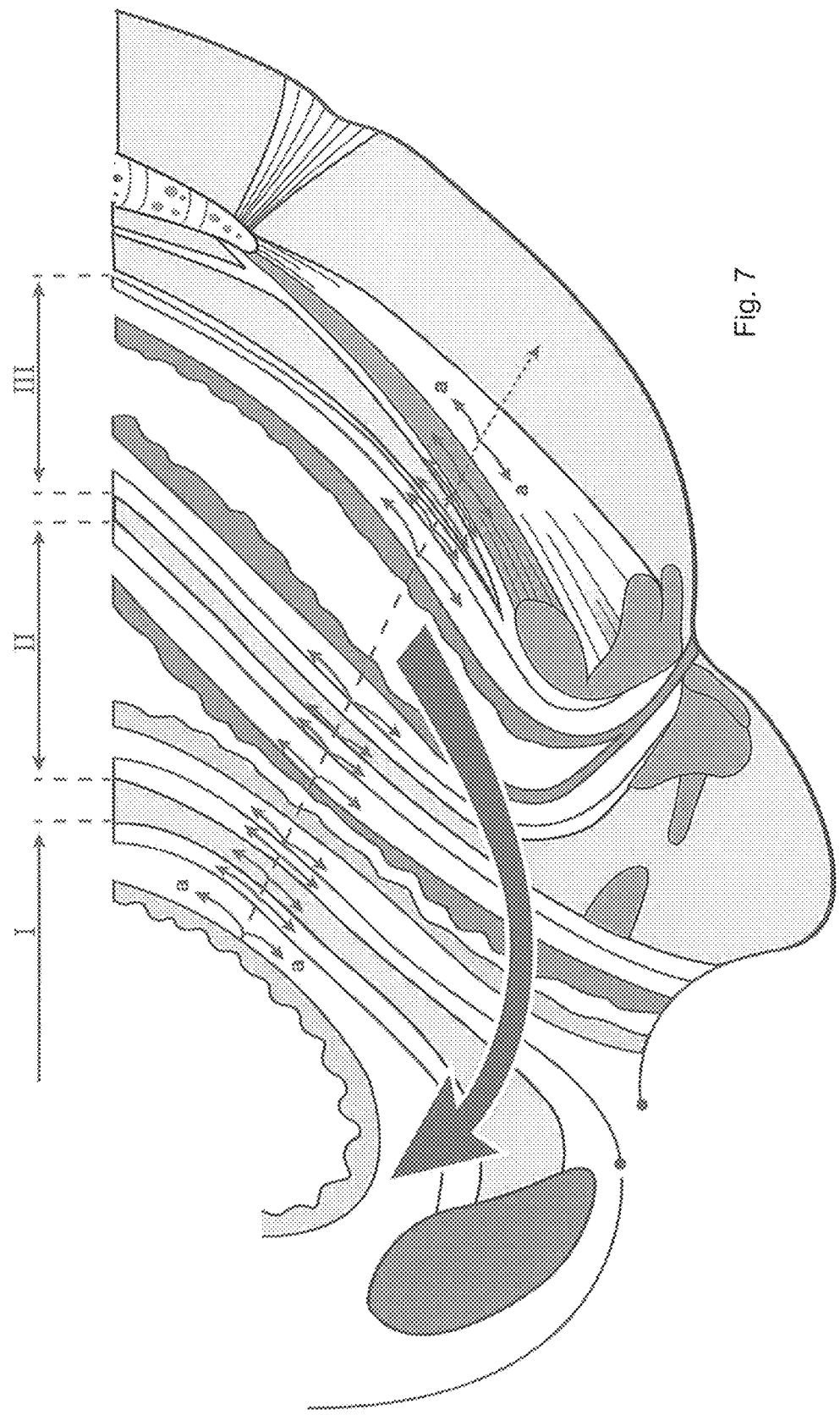

FIG. 7 comprises a curved arrow depicting the vectorial return of the forces in the small pelvis on the perineum.

FIG. 8 shows very schematically the effect of the holding device 100, to return the incident stress vector under the stress of a returned stress vector completing the vector return in FIG. 7.

In greater detail, the abdominal effort causes the organs to slide between each other (red arrow). The organs are elastic and held together by the soft connective tissue (frictional stresses). These movements, retained by the ligaments (pubourethral), cause the plicature of the tissues on one other, like the folding of a garden hose. This plicature stops the flow and is referred to as the functional area of the urethra.

If the connective tissues loosen, or the pubourethral ligaments are torn, there is nothing to hold the tissue together and the plication becomes non effective. Then the urethra remains straight, allowing the liquid to go through. (urinary incontinence due to urethro-vesical hypermobility).

The invention redirects the stresses so that this plicature can take place, (FIG. 8)

It consists of a rigid, narrow panel.

This panel is adjustable against the hard part of the small pelvis (the coccyx) at the rear.

Its position on the rear axis of rotation is adjustable to redirect the vectors of the reflected stresses to a variable height.

Its length is no more than the rear two-thirds of the perineum, in order to maintain mobility independent of the anterior third. Its width is no greater than the vaginal cleft between the labia minora, in order to maintain the independent mobility of the lateral parts of the perineum.

This short, narrow, adjustable rigid panel redirects the direction of friction due to the quasi-static flow of abdominal pressure. A plicature may recur, and the functional area and urethra (also called the sphincter) may become active.

LIST OF MAIN COMPONENTS

100 External directional support device
1 Cushion
11 Rigid panel
12 Envelope
13 Front attachment
14 Rear attachment
2 front straps
3 rear strap
31 End of the rear strap
4 Belt
41 Closing catch
42a,b Front attachment point/double ring
421 Hole
422, 423 Coupled rings
43 Rear attachment point, ring
44 Reinforcement
45 Rear reinforcement extension
441 Opening
5 Briefs combined with a retaining device
6 Briefs with integrated retaining device

The invention claimed is:

1. A device (100) for external support of a female urethra during effort, the device consisting of:
a rigid rectangular cushion (1) with a back strap (3) and two front straps (2), the rigid rectangular cushion (1) being configured to cover a posterior part of a perineum of a user; and
an abdominal belt (4) with one rear attachment point (43) and two front attachment points (42a,b) which adjustably receive respectively the back strap (3) and the two front straps (2), thereby being configured to hold the rigid rectangular cushion (1) against a rear and lower perineal area of the user, starting from a coccyx of the user;
the abdominal belt (4) being combined with briefs (6), and
the rigid rectangular cushion (1) being integrated in an intermediate part (62) of the briefs (6) connecting a front part (61) and a rear part (63) of the briefs (6).

* * * * *